(12) United States Patent
Yuz et al.

(10) Patent No.: US 11,495,344 B2
(45) Date of Patent: Nov. 8, 2022

(54) AUTOMATED SYSTEM AND METHOD FOR PROVIDING RADIOLOGICAL SECOND OPINIONS

(71) Applicant: USARAD HOLDINGS, INC., Fort Lauderdale, FL (US)

(72) Inventors: Michael Yuz, Oakland Park, FL (US); Alexander Krakopolsky, Oakland Park, FL (US); Dmitry Tochilnik, Oakland Park, FL (US)

(73) Assignee: USARAD HOLDINGS, INC., Fort Lauderdale, FL (US)

( * ) Notice: Subject to any disclaimer, the term of this patent is extended or adjusted under 35 U.S.C. 154(b) by 142 days.

(21) Appl. No.: 17/009,988

(22) Filed: Sep. 2, 2020

(65) Prior Publication Data
US 2022/0068464 A1 Mar. 3, 2022

(51) Int. Cl.
| | | |
|---|---|---|
| G16H 30/00 | (2018.01) | |
| G16H 30/20 | (2018.01) | |
| G16H 30/40 | (2018.01) | |
| G16H 50/20 | (2018.01) | |
| G06T 7/00 | (2017.01) | |
| H04L 67/02 | (2022.01) | |

(Continued)

(52) U.S. Cl.
CPC .......... *G16H 30/20* (2018.01); *G06Q 20/401* (2013.01); *G06T 7/0012* (2013.01); *G16H 30/40* (2018.01); *G16H 50/20* (2018.01); *H04L 9/0643* (2013.01); *H04L 67/02* (2013.01); *G06T 2207/10072* (2013.01); *H04L 9/50* (2022.05)

(58) Field of Classification Search
CPC ........ G16H 30/20; G16H 30/40; G16H 50/20; G06Q 20/401; G06T 7/0012; H04L 9/0643; H04L 9/50; H04L 67/02; G16T 2207/10072
See application file for complete search history.

(56) References Cited

U.S. PATENT DOCUMENTS 11,277,390 B2 * 3/2022 Verzun .................. H04L 63/102
2006/0026051 A1 2/2006 Rose
(Continued)

OTHER PUBLICATIONS

International Search Report and Written Opinion, dated Jan. 18, 2022, International Searching Authority, Application No. PCT/US2021/48264.

*Primary Examiner* — Khai M Nguyen
(74) *Attorney, Agent, or Firm* — Burr & Forman LLP; Jeffrey H. Kamenetsky (57) ABSTRACT

A computer-implemented method for providing a radiological opinion includes the steps of: (a) receiving an order for a radiological opinion by means of a web-based application accessible to a user; (b) launching an upload/scan application accessible to the user; (c) scanning a user-selected folder or drive for DICOM images; (d) parsing the DICOM images found in step (c); (e) uploading the DICOM images parsed in step (d); (f) routing the uploaded DICOM images to a picture archiving communication system; (g) generating a radiology order; (h) routing the radiology order to a radiology information system; (i) receiving a radiological opinion; (j) routing the radiological opinion to the user and (k) receiving electronic payment from the user following a successful upload of the radiological opinion, the electronic payment being governed by blockchain technology.

10 Claims, 5 Drawing Sheets

(51) Int. Cl.
  *H04L 9/06* (2006.01)
  *G06Q 20/40* (2012.01)
  *H04L 9/00* (2022.01)

(56) References Cited

U.S. PATENT DOCUMENTS

| | | | |
|---|---|---|---|
| 2007/0203748 A1* | 8/2007 | Rothpearl | G06Q 10/06 382/128 |
| 2008/0059237 A1 | 3/2008 | Koren | |
| 2008/0275729 A1 | 11/2008 | Taggart | |
| 2009/0177405 A1 | 7/2009 | Niggerbrugg | |
| 2009/0319291 A1 | 12/2009 | Noordvyk | |
| 2010/0042653 A1 | 2/2010 | Krishnan et al. | |
| 2010/0234691 A1 | 9/2010 | Iwano | |
| 2011/0093295 A1 | 4/2011 | Mankad | |
| 2012/0090043 A1 | 4/2012 | Twizere | |
| 2012/0323593 A1* | 12/2012 | Backhaus | G16H 80/00 705/2 |
| 2013/0060579 A1* | 3/2013 | Yu | H04L 63/06 705/3 |
| 2014/0119232 A1 | 5/2014 | Gurewitz et al. | |
| 2014/0119632 A1* | 5/2014 | Yuz | G16H 40/67 382/132 |
| 2017/0352158 A1 | 12/2017 | Raina | |
| 2020/0135326 A1 | 4/2020 | Averbach et al. | |

* cited by examiner

AUTOMATED SYSTEM AND METHOD FOR PROVIDING RADIOLOGICAL SECOND OPINIONS

STATEMENT REGARDING FEDERALLY SPONSORED RESEARCH OR DEVELOPMENT

Not Applicable

REFERENCE TO A SEQUENCE LISTING, TABLE OR COMPUTER PROGRAM LISTING APPENDIX

Not Applicable

BACKGROUND OF THE INVENTION

Field of the Invention

Embodiments of the present invention generally relate to teleradiology and more particularly to an automated system and method for providing radiological second opinions.

State of the Prior Art

Current practice in the healthcare industry, and particularly radiology, is for radiologists and other physicians to generate radiological images of the human body, or one or more parts of the human body, and to use these images for clinical purposes in the course of diagnosing or treating a disease or condition. The radiologist analyzes and interprets the images of the radiological films or other output and provides a diagnosis or prognosis of disease or condition with respect to the patient. Given the importance of the radiological diagnosis to a patient's health, well-being and progress in fighting the disease or condition of interest, it is frequently desirable for a patient to obtain a second opinion relating to the radiological images.

Oftentimes it is difficult for a patient or consumer to find and obtain a source for providing a second opinion regarding diagnosis and analysis of the radiological images. The problem has been ongoing for many years, with patients generally being required to visit the second radiologist in person in order to deliver the films or other media on which the data have been encoded in order for the second radiologist to render his opinion.

Much current practice involves a patient or consumer requesting a referral to a second radiologist from his or her first radiologist or perhaps from his or her existing healthcare provider, such as his or her primary healthcare physician, in order to obtain a second opinion or diagnosis regarding the radiological images. Other times, the patient or consumer might obtain the radiological images and associated information from the healthcare institution that generated the radiological images, whereupon the patient or consumer may provide those radiological images to one or more radiologists that the patient has identified by him or herself, so that one of these radiologists can provide a second opinion regarding the radiological images.

However, for many patients, especially those in remote locales, finding even a first radiologist may be a problem, let alone finding a second one who is qualified to interpret a radiology image. In most instances, seeking and obtaining another physician to provide a second opinion results in a secondary examination of the patient if the patient is geographically close to the second radiologist. This is unnecessary, costly, and inconvenient and may expose the patient to needless additional radiation exposure. Other times, due to the distance involved, and the fact that the patient may be elderly or infirm, and have difficulty traveling, the second opinion is never obtained from a second radiologist.

Furthermore, radiology has become an extremely complex specialty and usually one radiologist cannot be an expert in all areas. The imaging-industry knowledge base has dramatically expanded with the advent of MRI, multi-detector-row CT (MDCT), PET/CT, and the newly developing applications for these modalities. Keeping up with the latest advances is becoming a challenge for radiologists. No one radiologist can be an expert in everything, so radiology subspecialists have evolved—first as clinical experts (musculoskeletal, neuroradiology, nuclear medicine, and interventional), then as modality experts (MRI, CT, PET, and so forth), and later as experts in specialized clinical, modality, anatomy, and pathology areas. For these reasons, it is sometimes critical for a subspecialist to review a patient's study, especially if it is complicated.

An attempt to solve some of the problems associated with obtaining a radiological second opinion is described in U.S. Patent Application Publication No. 2009/0319291 entitled "Systems and Methods for Providing a Self-Service Mechanism for Obtaining Additional Medical Opinions Based on Diagnostic Images". A subscriber to a website may send or upload medical images and associated data to the website whereupon a list of physicians qualified to perform a second or subsequent read of the medical images is provided to the subscriber. The subscriber may select a physician from the list. Alternatively, a physician may log into a website portal when he/she is interested in performing second or subsequent reads of medical images and check for a message indicating that a subscriber has requested a second or subsequent read of the medical images. A first physician accepting the subscriber's request is assigned to perform the second or subsequent read of the medical images. In yet another alternative, physicians may be sent a message indicating that a subscriber has requested a second or subsequent read of the medical images and the first physician to respond to the subscriber is assigned the second or subsequent read. Finally, physicians may send bids to the subscriber indicating a bid or monetary amount to be charged by the physician for providing the second or subsequent read. The subscriber may select the physician offering the lowest bid. Once a physician is assigned or selected, a server processor retrieves the subscriber's medical images and associated data and sends these to the electronic device of the assigned or selected physician in an email message, a SMS message or the like. Alternatively, the physician may log in to a web site server and download the medical images and associated data from the memory of the server and store this data to a memory of the physician's electronic device.

The described systems and methods rely upon messaging (email, SMS and the like) between the physicians, the subscriber and the web server in the process of assigning or selecting the physician to perform the second or subsequent read of the subscriber's medical images. Furthermore, the server processor either sends the subscriber's images and associated data in an email message, a SMS message or the like or the physician must download the medical images and associated data to a memory of his/her electronic device.

In view of the problems associated with acquiring a second radiological opinion and the current state of the art, there remains a need for an automated system and method for providing radiological second opinions.

SUMMARY OF INVENTION

In accordance with one aspect of the invention, a computer-implemented method for providing a radiological opinion to a user comprises the steps of uploading at least one radiological image provided by the user, routing the uploaded at least one radiological image to a picture archiving communication system, routing an order message to a radiology information system, receiving a radiological opinion, routing the radiological opinion to the user; and, receiving electronic payment from the user following a successful upload of the radiological opinion, the electronic payment being governed by blockchain technology.

In accordance with another aspect of the invention, a computer-implemented method for providing a radiological opinion comprises the steps of receiving an order for a radiological opinion by means of a web-based application accessible to a user, launching an upload/scan application accessible to the user, scanning a user-selected folder or drive for DICOM images, parsing the DICOM images, uploading the parsed DICOM images, routing the uploaded DICOM images to a picture archiving communication system, generating a radiology order, routing the radiology order to a radiology information system, receiving a radiological opinion, and routing the radiological opinion to the user.

In accordance with yet another aspect of the invention, a system for providing a radiological opinion comprises a processor configured to serve a web-based application to a user's electronic device, scan and parse a user-selected folder or drive for DICOM images and/or studies, upload the parsed DICOM images and/or studies, route the DICOM images and/or studies to a picture archiving communication system, generate and transmit an HL7 radiology order to a radiology information system, receive an HL7 message from the radiology information system including the radiological second opinion, transform the HL7 message into a user-readable XML message, and send the user readable XML message to the user's electronic device.

In one of its aspects, the present invention provides an automated system for providing radiological second opinions. The system may be logically divided into a front-end, a middleware component and a back-end. The front-end includes a web-based application providing a patient (hereinafter also referred to as an XMRI.com customer or a SecondOpinions.com customer) with a user interface displayable on a patient's electronic device. The web-based application includes computer code executable by a middleware component processor. The web-based application allows the patient to create an account, upload medical images and associated data to the middleware component, provide for electronic payment in consideration for the radiological second opinion, and receive confirmations and the radiological second opinion from the middleware component.

The middleware component includes a hardware device such as a router or virtual base server (VMWARE, XEN) having a processor configured to execute computer code operable to: 1) serve the web-based application to the patient's electronic device; 2) scan a patient selected folder or drive for DICOM images and/or studies; 3) upload the patient DICOM images and/or studies; 4) receive electronic payment from the patient following the successful upload of the patient DICOM images and/or studies; 5) route the DICOM images and/or studies to the back-end; 6) receive confirmation from the back-end of receipt of the patient DICOM images and/or studies; 7) send the patient confirmation of the transmission of the patient DICOM images and/or studies to the back-end; 8) generate and transmit a radiology order to the back-end; 9) receive an HL7 message from the back-end including the radiological second opinion; and 10) transform and send the radiological second opinion to the patient's electronic device. The middleware component is connected to the back-end by means of an electronic network.

The back-end includes a PACS and a RIS connected to each other by an electronic network means or alternatively, a PACS/RIS combination. The PACS includes a processor that is operable to store the patient's DICOM images and/or studies and make these accessible to a pool of radiologists contracted to provide the radiological second opinions. The RIS includes a processor that is operable to provide an HL7 interface enabling communication between the RIS and the PACS and to manage a database for storing and distributing patient radiological reports, orders and other radiological data.

In another of its aspects, the present invention provides a computer-implemented method for automating the provision of radiological second opinions to a patient. The method includes the steps of: 1) a patient/customer submitting an order for a radiological second opinion by means of a web-based application accessible to the patient/customer on his/her electronic device; 2) launching an upload/scan application; 3) the patient/customer selecting a folder or drive including the DICOM images and/or study he/she wishes to have read; 3) scanning and parsing the patient/customer selected folder or drive for DICOM images and/or study; 4) the patient/customer selecting the DICOM images and/or study to upload; 5) uploading the patient/customer selected DICOM images and/or study; 6) determining if the upload of the patient/customer selected DICOM images and/or study was successful; 7) reloading the patient/customer selected DICOM images and/or study if the upload was unsuccessful; 8) following successful upload of the DICOM images and/or study, electronically charging the patient/customer for the radiological second opinion; 9) routing the uploaded DICOM images and/or study to a PACS; 10) receiving confirmation of receipt by the PACS of the DICOM images and/or study; 11) transmitting confirmation of receipt by the PACS of the DICOM images and/or study to the patient/customer; 12) generating and sending a radiology order to a RIS; 13) receiving a radiological second opinion; and 14) transmitting the radiological second opinion to the patient/customer.

The system and method of the invention utilize cloud computing concepts whereby the middleware component and the back-end do not require end user knowledge of their physical location. This enables synchronous communication with the patient/customer's electronic device at all times. The technology allows anyone who is authorized (such as the radiologist reading the patient's DICOM images and/or study) to access the data (such as the patient's DICOM images and/or study accessible on the PACS) at any time from any on-line source as well as to transmit the radiological second opinion to the RIS at any time. The data are mobile, transferrable and instantly accessible to those with the appropriate security keys. The key to enabling the portable interactivity of the invention is the ability to "sync up" the data between the middleware component and the back-end as well as providing access to the data.

There has been outlined, rather broadly, the more important features of the invention in order that the detailed description thereof that follows may be better understood, and in order that the present contribution to the art may be better appreciated. There are, of course, additional features of the invention that will be described below and which will form the subject matter of the claims appended herein.

In this respect, before explaining at least one embodiment of the invention in detail, it is to be understood that the invention is not limited in its application to the details of the configuration set forth in the following description or illustrated in the drawings. The invention is capable of other embodiments and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other systems and methods for carrying out the several purposes of the present invention. It is important, therefore, that the claims be regarded as including such equivalent systems and methods insofar as they do not depart from the spirit and scope of the present invention.

BRIEF DESCRIPTION OF THE DRAWING FIGURES

The present disclosure may be better understood and its numerous features and advantages made apparent to those skilled in the art by referencing the accompanying drawings wherein.

DETAILED DESCRIPTION OF A PREFERRED EMBODIMENT

The invention will now be described in sufficient detail to enable one skilled in the art to make and use the invention. As used herein, the following terms have the meanings stated:

RADIOLOGIST—a medical specialist using imaging to diagnose disease or conditions visualized within the human body.

TELERADIOLOGY—radiology concerned with the transmission of digital medical images such as X-rays, CAT scans, sonograms, and the like over electronic networks with interpretation of the transmitted images for diagnostic purposes.

PACS—an acronym for "Picture Archiving Communication System" which is a medical imaging technology providing storage of, and convenient access to, images from multiple modalities, namely various source machine types. A PACS may provide remote access to the stored images.

RIS—an acronym for "Radiology Information System" which is a computerized database used to store and distribute patient radiological reports and other radiological data. A RIS includes an HL7 interface enabling communication between the RIS and the PACS.

RIS/PACS combination—an acronym for a radiology information system/picture archiving and communication system that is integrated internally.

HL7—an acronym for "Health Level 7" which is an ANSI accredited standard for electronically defining clinical and administrative data in the healthcare industry from Health Level 7 International.

DICOM—an acronym for "Digital Imaging and Communications in Medicine" which a standard for handling, storing, printing and transmitting information in the medical imaging field.

Folder—a digital file system in which groups of computer files and other folders can be kept and organized.

DICOM Folder—a folder containing radiological images in DICOM format which can be stored on compact disks, digital video disks, flashdrives, computer drives or in virtual storage.

XMRI.com or SecondOpinions.com Customer—a patient or patient's representative such as a clinician, radiologist, a radiologist facility, other medical professional and medical facility, legal guardian, law firm and legal professionals as well as the patient's insurance company.

Figure 1:
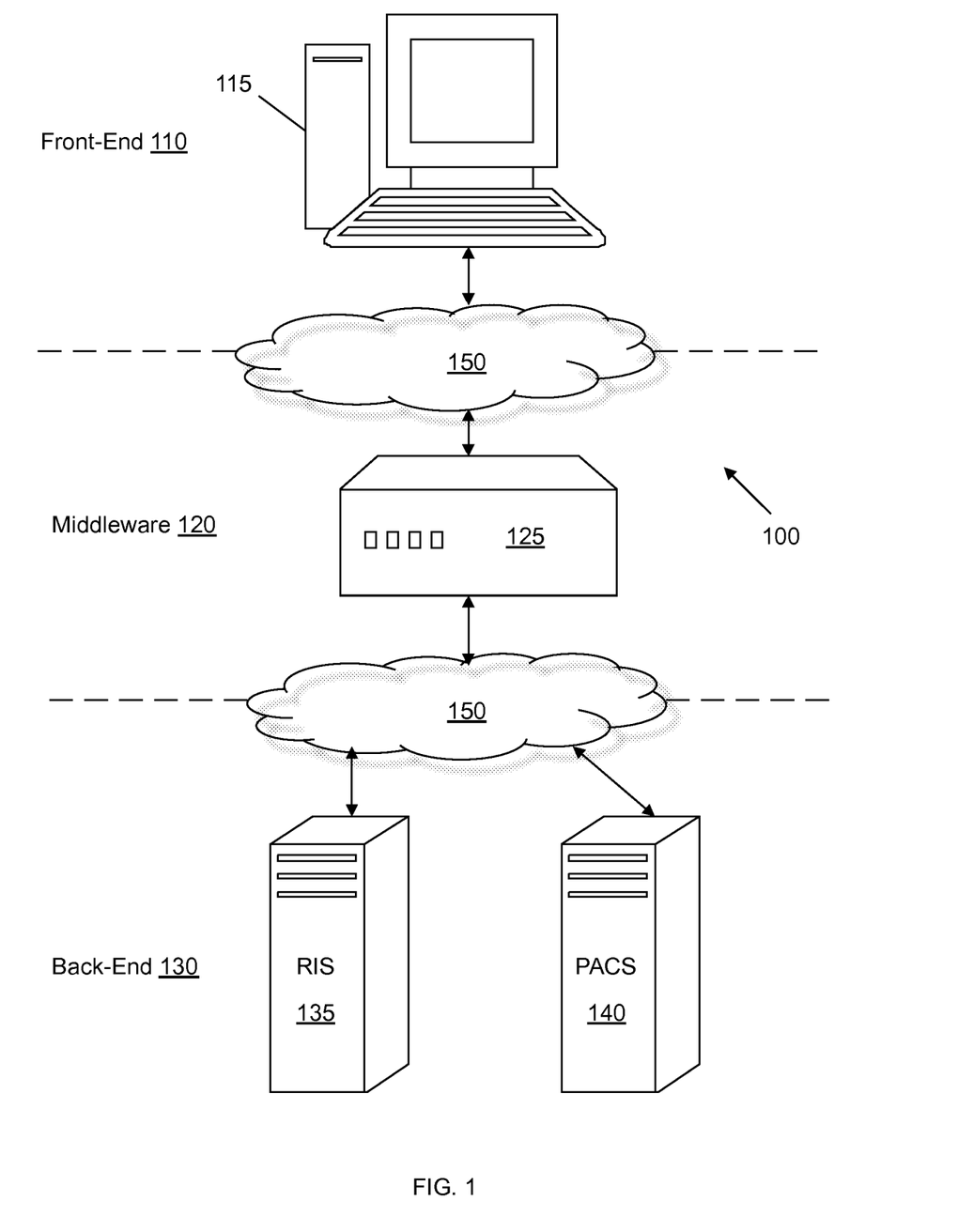
FIG. 1 is a schematic representation of an automated system for providing radiological second opinions in accordance with the invention.
Figure 2:
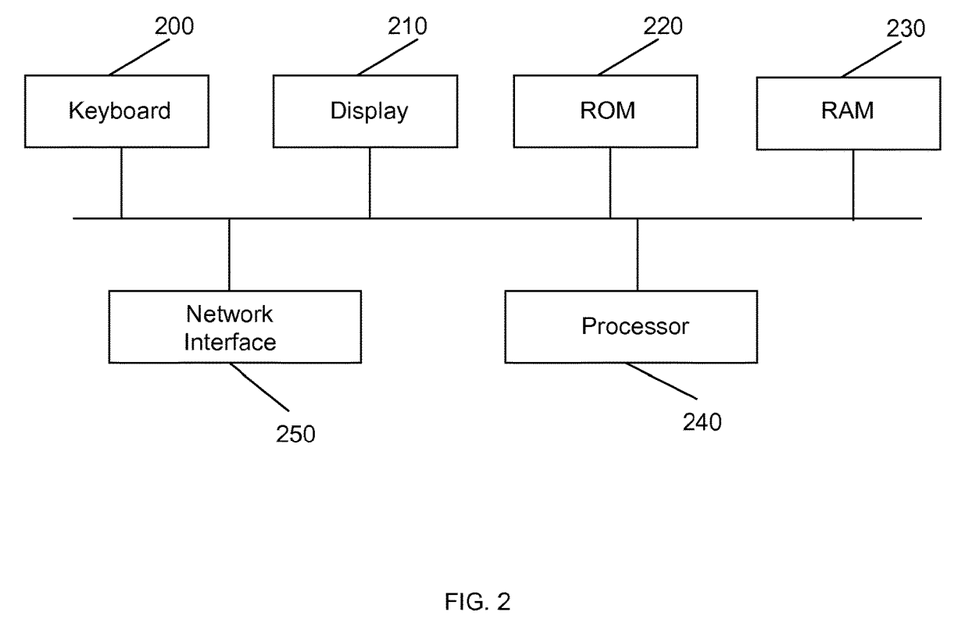
FIG. 2 is a schematic representation of a hardware device in accordance with the invention.

In accordance with one aspect of the invention, an automated system for providing radiological second opinions generally designated 100 and shown in FIG. 1 may be divided into three logical components: a front-end 110, a middleware component 120 and a back-end 130. The front-end 110 includes a web-based application providing a patient with a user interface displayable on a patient's electronic device 115. The patient's electronic device 115 is shown as a desktop computer for illustrative purposes only and can be any electronic device capable of running the web-based application including a laptop computer, a hand-held computer and a smart phone. With reference to FIG. 2, the patient's electronic device 115 includes memory (ROM 220 and RAM 230) for storing computer code capable of being processed by a processor 240. The patient's electronic device 115 may also include conventional components such as a keyboard 200, a display 210, a touchscreen (not shown) and a network interface 250 capable of communicatively connecting the patient's electronic device 115 to the internet 150 or other electronic network and therethrough to the middleware component 120.

The web-based application allows the patient to create an account with an XMRI.com or SecondOpinions.com website, upload medical images and associated data to the middleware component 120, provide for electronic payment in consideration for the radiological second opinion, and receive confirmations and the radiological second opinion from the middleware component 120.

In one embodiment, the present disclosure utilizes block-chain technology to govern disputes, govern electronic payments, and establish communication directly between parties without third-party intermediaries. Blockchains are decentralized, peer-to-peer networked databases that can store and authenticate a ledger of assets and asset transactions. Blockchain technology allows transactions to occur without a third-party intermediary. Blockchain technology uses smart contracts to resolve disputes. Smart contracts are computer programs designed to act as self-executing contracts that implement aspects of a transaction where the terms of the agreement between buyer and seller are directly written into lines of software code. The code and the agreements exist across a distributed, decentralized blockchain network.

The present disclosure allows for transactions to take place across a blockchain database. For example, any electronic payment that is sent by the patient/customer following the successful upload of the patient DICOM images and/or studies or when electronic payment is provided in consideration for a radiological second opinion, can be governed by blockchain technology, specifically using a smart contracts concept, which allows for instantaneous payment.

Further, the present disclosure allows for all radiological second opinions to be stored in a blockchain database.

The middleware component 120 includes a hardware device such as a router or virtual base server (VMWARE, XEN) having a processor configured to execute computer code that implements the automated method for providing radiological second opinions as described hereinbelow. Relevant features of the middleware component 120 are described in non-provisional patent application Ser. No. 13/385,509 entitled "User-configurable Radiological Data Transformation, Routing and Archiving Engine" filed by one of the co-inventors hereof, the disclosure of which is incorporated herein by reference in its entirety. The middleware component 120 is communicatively connected to the back-end 130 by means of the internet 150 or other electronic network.

In implementing the method of the invention, the middleware component 120 executes computer code operable to: 1) serve the web-based application to the patient's/customer's electronic device; 2) scan and parse a patient/customer selected folder or drive for DICOM images and/or studies; 3) upload the parsed patient/customer DICOM images and/or studies; 4) receive electronic payment from the patient/customer following the successful upload of the patient/customer DICOM images and/or studies; 5) route the patient/customer DICOM images and/or studies to the back-end; 6) receive confirmation from the back-end of receipt of the patient/customer DICOM images and/or studies; 7) send the patient/customer confirmation of the transmission of the patient DICOM images and/or studies to the back-end; 8) generate and transmit an HL7 radiology order to the back-end; 9) receive an HL7 message from the back-end including the radiological second opinion; and 10) transform and send the radiological second opinion to the patient's/customer's electronic device.

The back-end 130 includes a RIS 135 and a PACS 140. The RIS 135 and the PACS 140 are connected to the internet 150 or other electronic network. The PACS 140 provides storage and access to the patient's DICOM images and/or study to one or more members of a pool of radiologists contracted to render the radiological second opinion. The RIS 135 includes an HL7 interface enabling communication between the RIS 135 and the PACS 140. The RIS 135 stores an HL7 order for a radiological second opinion generated by the middleware component 120 and makes the HL7 order available to radiologist members of the pool. The RIS 135 may implement rules including assigning the order to the first radiologist in the pool to respond or making the HL7 order only viewable to certain radiologists based on criteria including the nature of the DICOM images and/or study, the qualifications of the radiologist and the subspecialty of the radiologist. In certain circumstances, such as where the customer requests that a certain radiologist perform the read of the DICOM images and/or study, the rules may be manually over-ridden to accommodate the customers' request. The RIS 135 is also operable to send an HL7 message to the middleware component 120 including the radiological second opinion.

In accordance with another aspect of the invention, an automated method 300 (FIGS. 3A-3C) for patients desiring to obtain a second opinion regarding radiological analysis or diagnosis provided by a radiologist is disclosed. In the practice of the method 300 the radiological second opinion is provided by a radiology subspecialist.

Figure 3A:
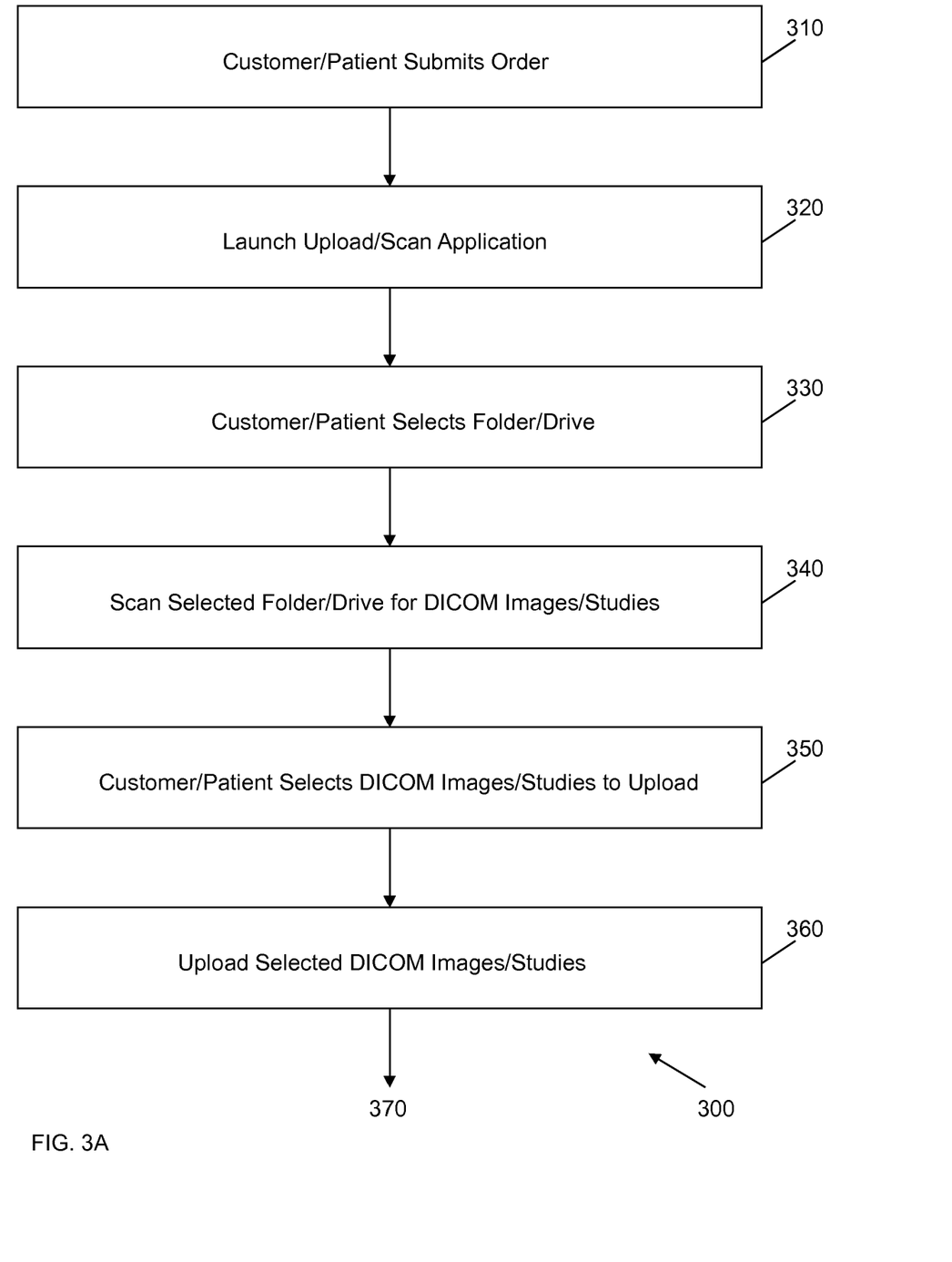
FIGS. 3A through 3C show a flow diagram of an automated method for providing radiological second opinions in accordance with the invention.
Figure 3B:
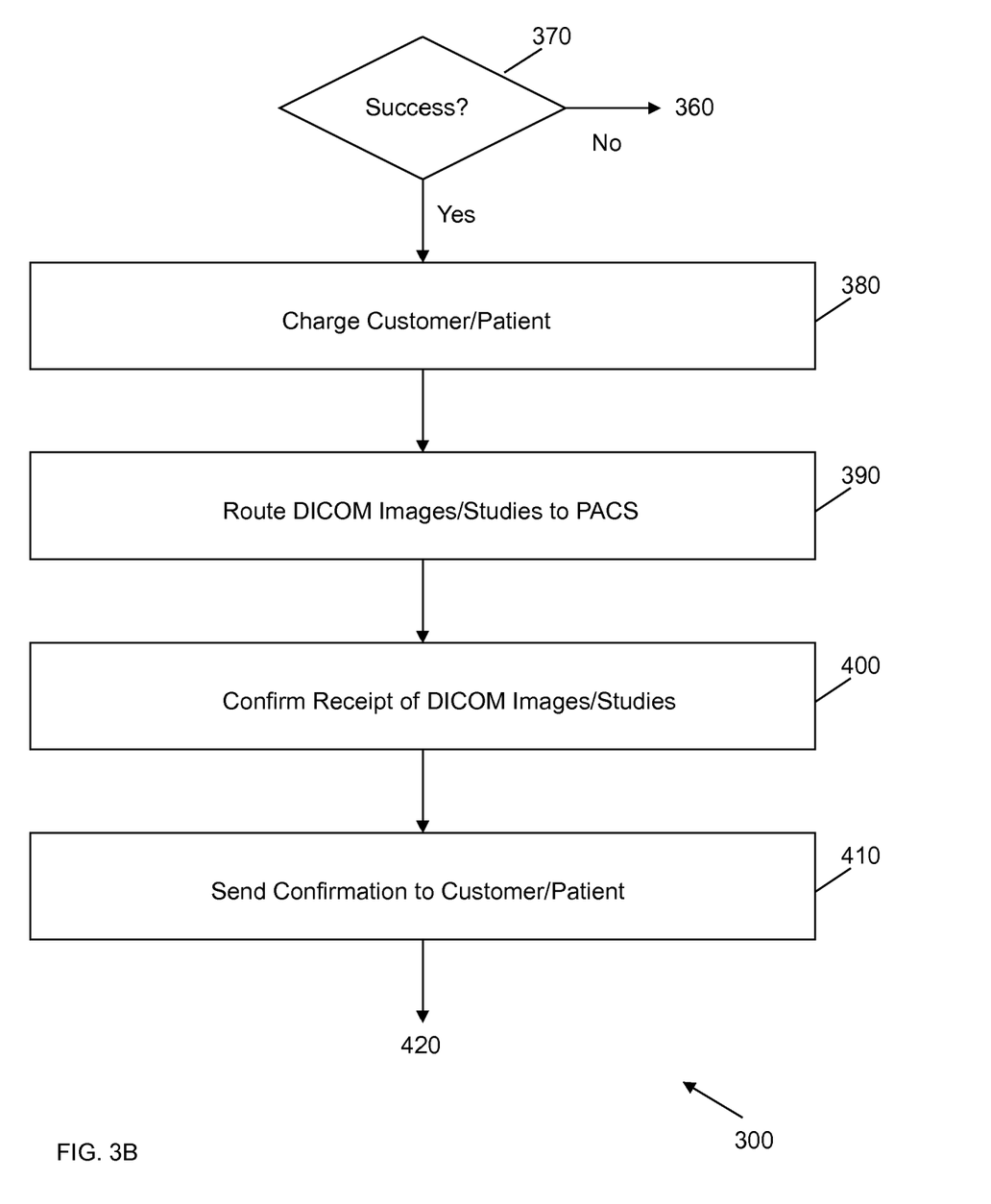
Figure 3C:
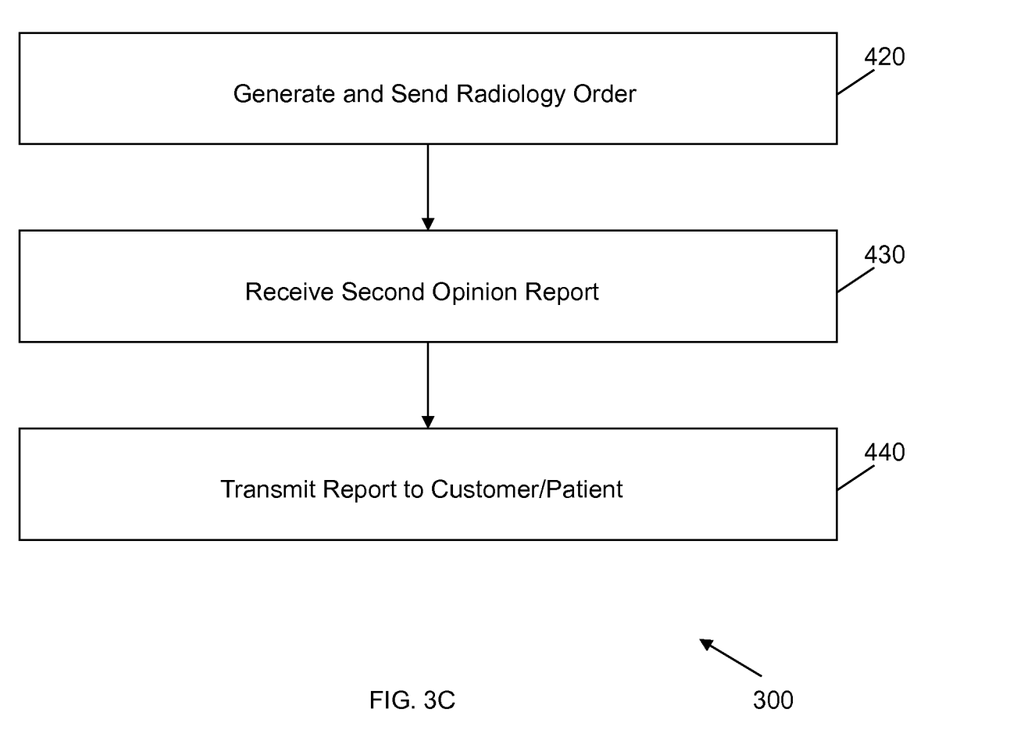

The method 300 may begin with a patient desiring a second opinion accessing the XMRI.com website or SecondOpinions.com website from their electronic device 115 and creating an account. Account creation may include providing information related to the patient such as his/her name, address, date of birth, physicians name, radiologists name, preference as to which radiologist from the pool of radiologists is to perform the read, and credit card information. Following the creation of an account the patient becomes an XMRI.com customer. It is expected that the XMRI.com customer is in possession of his/her DICOM images and/or study and that this data is stored on a digital media such as a CD, DVD, flash drive, computer hard drive or a cloud storage device.

In accordance with the method 300 of the invention, the XMRI.com customer submits 310 an order for a radiological second opinion by means of a web-based application provided by the XMRI.com or SecondOpinions.com website. The web-based application is accessible to the XMRI.com customer on his/her electronic device 115. An upload/scan application is then launched 320 and displayed to the XMRI.com customer on his/her electronic device 115. Next the XMRI.com customer selects 330 a folder or drive storing the DICOM images and/or study he/she wishes to have read and the XMRI.com customer selected folder or drive is scanned 340 and parsed for DICOM images and/or studies. The XMIR.com customer then selects 350 the DICOM images and/or studies to be uploaded from the data recognized in the step 340 and the selected DICOM images and/or study are uploaded 360 to the middleware component 120 via a secure web connection.

A determination is next made 370 if the upload of the XMRI.com customer selected DICOM images and/or study was successful. If the upload was not successful, then the XMRI.com customer selected DICOM images and/or study is reloaded 360. Upon successful upload of the customer selected DICOM images and/or study the XMRI.com customer is electronically charged 380 for the radiological second opinion. Charges for the radiological second opinion are made on a fixed-fee basis and generally depend upon the nature of the read. The charges are provided to the XMRI.com customer by the web-based application.

The uploaded DICOM images and/or study are next routed 390 to the back-end 130 and stored in the PACS 140. Receipt by the PACS 140 of the DICOM images and/or study is next confirmed 400 by the middleware component 120 and a confirmation sent 410 to the XMRI.com customer. An HL7 radiology order is then generated and sent 420 to the back-end 130 and stored in the RIS 135. The radiology order and the related DICOM images and/or study then become available to a pool of radiologists contracted to provide the second opinion. Preferably the pool of radiologists includes ABR certified radiologists trained at top U.S. institutions. The pool of radiologists further preferably includes radiologists who are fellowship trained and who have additional CAQ certifications. The pool of radiologists also preferably includes radiologists having expertise in subspecialties including neuroradiology, musculoskeletal, body, emergency radiology, pediatrics, PET/CT and oncologic imaging and cardiac CT angiography. Each of the pool of radiologists preferably provides the administrators of the XMRI.com or SecondOpinions.com website with their schedule of availability.

In one embodiment, processor 240 automatically selects one or more radiologists from the pool of radiologists to render a second opinion. This selection can be based on radiologist criteria and expertise discussed above.

In another embodiment, artificial intelligence (AI")" algorithms are used to help radiologists analyze the DICOM images and/or study faster and more accurately.

The RIS 135 may implement rules including assigning the order to the first radiologist in the pool of available radiologists to respond or making the HL7 order only viewable to certain radiologists based on criteria including the nature of the DICOM images and/or study, the qualifications of the radiologist and the subspecialty of the radiologist. In certain circumstances, such as where the customer requests that a certain radiologist perform the read of the DICOM images and/or study, the rules may be manually over-ridden to accommodate the customers' request. The RIS 135 is also operable to send an HL7 message to the middleware component 120 including the radiological second opinion.

The radiological second opinion (in the form of an HL7 message) is received 430 in the middleware component 120 and transmitted 440 to the XMRI.com customer (in the form of an XML message). The XMRI.com customer may view the radiological second opinion by means of his/her electronic device 115.

The practice of the method of the invention does not establish any doctor-patient relationship. The method and system of the invention are used only to provide second opinions as to interpretation and diagnoses of conditions appearing on visually discernable radiological media.

The system and method of the invention advantageously automate all of the steps comprising the provision of a radiological second opinion with the exception of the radiologist's read of the patient's images. The middleware component is operable to route the uploaded DICOM images and/or studies to the PACS and transmit the HL7 order to the RIS. In combination, the PACS and RIS provide the pool of radiologists (or a subset of the pool of radiologists) with the necessary notice of the order and accessibility to the DICOM images and/or studies. The middleware component is further operable to receive the HL7 message including the report from the RIS, to transform the HL7 message into a patient-readable format and to transmit the report to the patient.

Although the automated system and method for providing radiological second opinions has been described with reference to the particular embodiments, it is noted that equivalents may be employed and substitutions made herein without departing from the scope of the invention. For example, while the term "radiological second opinions" has been used throughout the description of the invention, it is clear that the system and method of the invention may be applied to other than second opinions including additional opinions and subsequent opinions. Furthermore, the middleware component may scan and upload all related DICOM images whether part of a single study or multiple studies. In addition, the back-end has been described as having distinct PACS and RIS servers but could include a PACS/RIS combined server capable of providing both PACS and RIS functionality in a single machine.

We claim:

1. A computer-implemented method for providing a radiological opinion comprising the steps of:
   (a) receiving an order for a radiological opinion by means of a web-based application accessible to a user;
   (b) launching an upload/scan application accessible to the user;
   (c) scanning a user-selected folder or drive for DICOM images;
   (d) parsing the DICOM images found in step (c);
   (e) uploading the DICOM images parsed in step (d);
   (f) routing the uploaded DICOM images to a picture archiving communication system;
   (g) generating a radiology order;
   (h) routing the radiology order to a radiology information system;
   (i) receiving a radiological opinion;
   (j) routing the radiological opinion to the user; and
   (k) receiving electronic payment from the user following a successful upload of the radiological opinion, the electronic payment being governed by blockchain technology.

2. The computer-implemented method of claim 1, wherein uploading the DICOM images parsed in step (d) comprises uploading the DICOM images to a DICOM router.

3. The computer-implemented method of claim 2, wherein generating a radiology order comprises generating an HL7 order in the DICOM router.

4. The computer-implemented method of claim 2, wherein receiving a radiological opinion comprises receiving an HL7 report message in the DICOM router.

5. The computer-implemented method of claim 4, wherein routing the radiological opinion to the user comprises transforming the HL7 reportmessage into an XML message and routing the XML message to the user.

6. The computer-implemented method of claim 1, wherein receiving the radiological opinion comprises receiving an HL7 report message from one of a pool or radiologists having access to the radiology information system and to the picture archiving communication system.

7. The computer-implemented method of claim 1, further comprising electronically charging the user for the radiological opinion following step (e).

8. The computer-implemented method of claim 1, further comprising receiving confirmation from the picture archiving communication system of receipt of the uploaded DICOM images following step (f).

9. The computer-implemented method of claim 8, further comprising sending confirmation of the receipt by the picture archiving communication system to the user.

10. An automated system for providing a radiological opinion comprising:
    a front-end component, a middleware component and a back-end component;
    the front-end component configured to provide to a patient a web-based application on a user interface of the patient's electronic device, the web-based application including a computer code executable by a processor of the middleware component;
    the processor of the middleware component configured to:
      execute computer code operable to serve the web-based application to the patient's electronic device;
      scan a patient selected folder or drive for DICOM images and/or studies;
      upload the patient DICOM images and/or studies;
      receive electronic payment from the patient following a successful upload of the patient DICOM images and/or studies, the electronic payment being governed by blockchain technology;
      route the DICOM images and/or studies to the back-end component;
      receive confirmation from the back-end component of receipt of the patient DICOM images and/or studies;
      send the patient confirmation of the transmission of the patient DICOM images and/or studies to the back-end component;
      generate and transmit a radiology order to the back-end component;
      receive an HL7 message from the back-end component including the radiological second opinion; and transform and send the radiological second opinion to the patient's electronic device; and the back-end component comprising:
- a Picture Archiving Communication System (PACS), the PACS including a processor operable to store the patient's DICOM images and/or studies and make these accessible to a pool of radiologists contracted to provide the radiological second opinions; and
- a Radiology Information System (RIS) connected to the PACS by an electronic network, the RIS including a processor operable to provide an HL7 interface enabling communication between the RIS and the PACS and to manage a database for storing and distributing patient radiological reports, orders and/or other radiological data.

* * * * *